United States Patent [19]

Satoh et al.

[11] Patent Number: 5,011,949

[45] Date of Patent: Apr. 30, 1991

[54] ASCORBIC ACID DERIVATIVE

[75] Inventors: Toshio Satoh; Yasunori Niiro; Hisao Kakegawa; Hitoshi Matsumoto, all of Tokushima, Japan

[73] Assignee: Nippon Hypox Laboratories, Inc., Tokyo, Japan

[21] Appl. No.: 382,771

[22] Filed: Jul. 20, 1989

[51] Int. Cl.$^5$ .................. C07D 307/33; C07D 307/06
[52] U.S. Cl. ..................................... 549/315; 549/448
[58] Field of Search ................ 549/315, 448; 514/474

[56] References Cited

FOREIGN PATENT DOCUMENTS 0146121 6/1985 European Pat. Off. .

Primary Examiner—Frederick E. Waddell
Assistant Examiner—Amelia A. Owens
Attorney, Agent, or Firm—Nixon & Vanderhye

[57] ABSTRACT

This invention relates to a novel ascorbic acid derivative having excellent antioxidant action, particularly eliminating action on superoxides and a process for preparing the same.

Furthermore, this invention also relates to a novel antioxidant comprising the aforementioned novel ascorbic acid derivative or other known ascorbic acid derivatives.

7 Claims, No Drawings

ASCORBIC ACID DERIVATIVE

BACKGROUND OF THE INVENTION
(1) Field of the Invention

This invention relates to an ascorbic acid derivative, a process for preparing the same and an antioxidant comprising an ascorbic acid derivative. (2) Prior Art Ascorbic acid has antioxidant action and is used for the purpose of preventing browning of foods, retaining flavor or freshness of foods or the like.

Ascorbic acid, however, is susceptible to decomposition and sometimes hard to produce the above-mentioned effects over a long period.

SUMMARY OF THE INVENTION

It is, therefore, a first object of this invention to provide a novel ascorbic acid derivative eliminating the aforementioned disadvantages of the ascorbic acid. It is a second object of this invention to provide a process for preparing the aforesaid novel ascorbic acid derivative. It is further a third object of this invention to provide an antioxidant comprising an ascorbic acid derivative.

The first object of this invention has been achieved by an ascorbic acid derivative represented by the general formula (Ia):

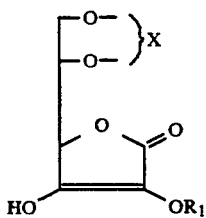
(Ia)

wherein $R_1$ is an alkylcarbonylalkyl group and X is two hydrogen atoms or $=C(CH_3)_2$.

The second object of this invention has been accomplished by a process for preparing an ascorbic acid derivative represented by general formula (Ia):

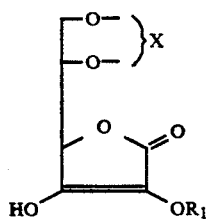
(Ia)

wherein $R_1$ is an alkylcarbonylalkyl group and X is two hydrogen atoms or $=C(CH_3)_2$, which comprises subjecting a compound represented by general formula (IIa):

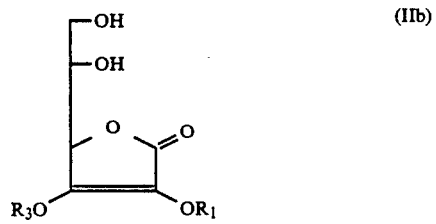
(IIa)

wherein $R_1$ has the same significance as above and $R_3$ is an arylalkyl group, or a compound represented by general formula (IIb):

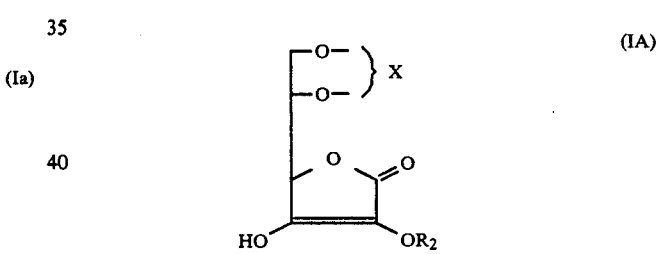
(IIb)

wherein $R_1$ and $R_3$ have the same significances as above, obtained by treating a compound of formula (IIa) with an acid, to catlaytic reduction.

Furthermore, the third object of this invention has been achieved by an antioxidant comprising an ascorbic acid derivative represented by general formula (IA):

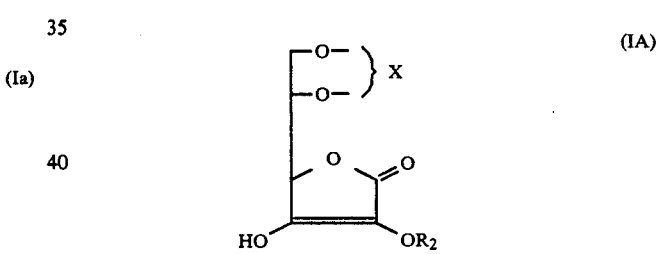
(IA)

wherein $R_2$ is a group selected from the group consisting of an alkylcarbonylalkyl group, an alkyl group, an aralkyl group, a hydroxycarbonylalkyl group, an alkoxycarbonylalkyl group and an alkylcarbonylalkyl group and X represents two hydrogen atoms or $=C(CH_3)_2$.

The group $R_1$ in the general formula (Ia) representing the novel ascorbic acid derivative of this invention is different in the number of substituent groups defined therein from the group $R_2$ in the general formula (IA) representing the ascorbic acid derivative constituting the antioxidant of this invention. Although the group $R_1$ has one substituent group, the group $R_2$ has the total five substituent groups including the one. This means that ascorbic acid derivatives which are not novel can also be used as the antioxidant of this invention.

The novel ascorbic acid derivative of this invention is initially explained hereinafter.

The novel ascorbic acid derivative of this invention is represented by general formula (Ia):

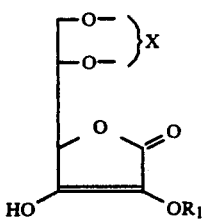
(Ia)

wherein $R_1$ is an alkylcarbonylalkyl group.

Examples of the alkylcarbonylalkyl group herein include groups represented by general formula:

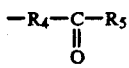

wherein $R_4$ is an alkylene group which may optionally have a branched chain and $R_5$ is an alkyl group which may optionally have a branched chain. Particularly preferred alkylcarbonylalkyl groups are —$CH_2$—CO—$CH_3$, $CH_2$—CO—$C_2H_5$ and the like.

The novel ascorbic acid derivative of this invention has excellent antioxidant action and can be preferably used food antioxidants or beautifying and whitening cosmetics.

The novel ascorbic acid derivative of this invention is an extremely specific compound in that it has the ability to eliminate superoxides having the possibility of damaging biomolecules and tissues, and application as a medicine is also considered for treating diseases derived from such superoxides.

The process for preparing the novel ascorbic acid derivative represented by the above-mentioned general formula (Ia) of this invention is explained hereinafter.

In the process of this invention, a compound represented by general formula (IIa):

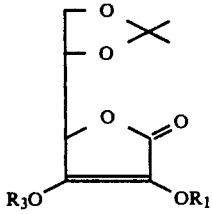
(IIa)

wherein $R_1$ is an alkylcarbonylalkyl group and $R_3$ is an arylalkyl group, or a compound represented by general formula (IIb):

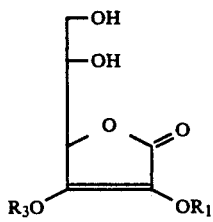
(IIb)

wherein $R_1$ and $R_3$ have the same significances as above, obtained by treating a compound of formula (IIa) with an acid, is used as a starting material.

The compound represented by the general formula (IIa) is obtained by treating 5,6-O-isopropylideneascorbic acid, synthesized from ascorbic acid by a conventional method and represented by formula:

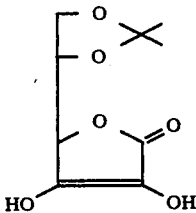

with an aryl alkyl halide (for example, benzyl halide) to aryl alkyl etherify (for example, benzyl etherify) the hydroxyl group at the 3-position to provide a 3-O-arylalkyl-5,6-O-isopropylideneascorbic acid (for example, 3-O-benzyl-5,6-O-isopropylideneascrobic acid) represented by the formula:

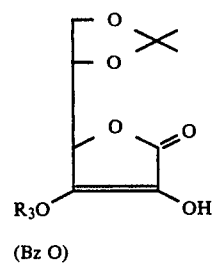

(Bz O)

and thereafter treating the resulting compound with an organic halide represented by the general formula:

$R_1$—Hal wherein $R_1$ is an alkylcarbonylalkyl group and Hal is a halogen atom.

Catalytic reduction of the compound represented by the general formula (IIa) or (IIb) which is a starting material is then carried out by using, for example, palladium-carbon powder in a hydrogen gas stream. The conditions of the catalytic reduction are suitably selected from those used for ordinary catalytic reductive reaction.

If the compound represented by the general formula (IIa) is used as the starting material, a compound represented by general formula (Ia), wherein X is $=C(CH_3)_2$, i.e. the compound represented by general formula:

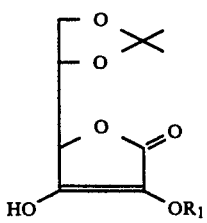

is obtained.

If the compound represented by general formula (IIb) is used as the starting material, a compound represented by the general formula (Ia) wherein X is two hydrogen atoms, i.e. the compound represented by the general formula:

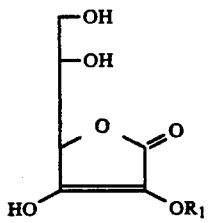

is obtained.

The antioxidant of this invention is explained hereinafter.

The antioxidant of this invention comprises an ascorbic acid derivative represented by the general formula (IA):

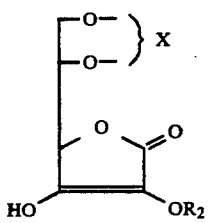

The group $R_2$ in the formula (IA) is within a wider scope than the group $R_1$ in the general formula (Ia) representing the novel ascorbic acid derivative as described above, and therefore the ascorbic acid derivative represented by the general formula (IA) includes also known compounds.

Thus, the group $R_2$ includes the same one substituent group as the group $R_1$, i.e. alkylcarbonylalkyl group, besides this, further four substituent groups of alkyl group, aralkyl group, hydroxycarbonylalkyl group and alkoxycarbonylalkyl group. The term "alkyl" in the aforementioned substituent groups means a straight or branched alkyl group. The term "alkoxy" means an alkoxy group consisting of a straight or branched alkyl group and an oxygen atom.

Such an ascorbic acid derivative represented by general formula (IA) has the ability to eliminate radicals and is preferably used as an antioxidant. It is excellent in the ability thereof to remove superoxides.

EXAMPLES

Examples of this invention are explained hereinafter.

Preparation example 1

Preparation of novel ascorbic acid derivative (Ia) wherein X is a group $=C(CH_3)_2$ (1) Synthesis of L-5,6-O-isopropylideneascorbic Acid Ascorbic acid in an amount of 180 g was stirred in 750 ml of acetone and warmed to 40° C. Acetyl chloride in a volume of 20 ml was added, and stirring was continued to form a slurry layer. After 3 hours, the slurry layer was cooled with ice to collect deposited precipitates by filtration. The resulting precipitates were washed with a mixture of cold acetone-n-hexane (3:7) on a funnel and dried with silica gel under reduced pressure.

Recrystallization from acetone was then carried out to provide 190 g of the title compound L-5,6-O-isopropylideneascrobic acid (melting point: 206°-208° C.).

(2) Synthesis of L-3-O-benzyl-5,6-O-isopropylideneascorbic Acid

In 30 ml of dimethyl sulfoxide, was dissolved 4.32 g of the compound obtained in (1). Sodium hydrogencarbonate in an amount of 1.66 g was added, and the resulting solution was stirred. After 30 minutes, 3.76 g of benzyl bromide was added, and the obtained solution was warmed to 50° C. After warming the solution for 20 hours, 100 ml of distilled water and ethyl acetate (100 ml×2) were added to shake the reaction solution. Organic layers were combined, washed with water, shaken with saturated sodium chloride solution and dried over sodium sulfate. An oily substance obtained by concentrating under reduced pressure was subjected t silica gel column chromatography and eluted with benzene-ethyl acetate to provide the title compound L-3-O-benzyl-5,6-O-isopropylideneascorbic acid (melting point: 105°-106° C.).

(3) Synthesis of L-3–0-benzyl-5,6O-isopropylidene-2-O-methylcarbomethylascorbic Acid In 20 ml of dimethyl sulfoxide, was dissolved 2.66 g of the compound obtained in (2). Potassium carbonate in an amount of 1.32 g was added thereto and the resulting mixture was stirred. Chloroacetone in an amount of 0.88 g was added thereto, and the resulting solution was stirred at room temperature for 20 hours. To the reaction solution, distilled water (100 ml) and ethyl acetate (100ml×2) were added to carry out shaking. Organic layers were combined, washed with water and dried over sodium sulfate. The obtained solution was concentrated under reduced pressure, and the resulting oily substance was subjected to silica gel column chromatography and eluted with benzene-ethyl acetate to afford 2.04 g of the title compound L-3-O-benzyl-5,6-O-isopropylidene-2-O-methylcarbomethylascorbic acid (oily substance MS M+ −15−347).

(4) Synthesis of L-5,6-O-isopropylidene-2-O-methylcarbomethylascorbic Acid

In 20 ml of ethyl acetate, was dissolved 2.00 g of the compound obtained in (3). To the resulting solution, was added 0.60 g of 10% palladium carbon powder to carry out catalytic reduction in a hydrogen gas stream. Insoluble materials were filtered off, and the filtrate was concentrated under reduced pressure. The obtained white precipitates were recrystallized from ethyl acetate-petroleum ether to provide 1.64 g of the title compound L-5,6-O-isopropylidene-2-O-methylcarbomethylascorbic acid (corresponding to compound No. 206 in Table-1).

Preparation Referential Example 1

Preparation of Other Ascorbic Acid Derivatives Included in the Ascorbic Acid Derivative (IA) Wherein X is a Group $=C(CH_3)_2$ Procedures were followed in the same manner as in Preparation example 1 to afford ascorbic acid derivatives designated as compound Nos. 201, 202, 203, 204 and 205 in Table-1.

TABLE 1

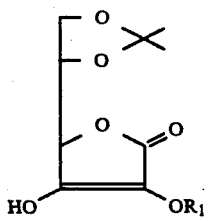

| Compound No. | $R_1$ | mp (°C.) | 90 mHz - NMR δ value |
|---|---|---|---|
| 201 | $CH_2CH_2CH_2CH_3$ | 91.5 | 0.91 (3H, m) 1.29 (6H, s) 1.53 (4H, m) 4.14 (5H, m) 4.57 (H, d, 3Hz) |
| 202 | $(CH_2)_3COOC_2H_5$ | Oily substance | 1.22 (3H, t) 1.37 (3H, s) 1.40 (3H, s) 2.17 (2H, m) 2.48 (2H, m) |
| 203 | $(CH_2)_3COOH$ | (105)-135-145 | 1.30 (6H, s) 1.95 (2H, m) 2.47 (2H, t) 4.12 (5H, m) 4.77 (H, d, 3Hz) |
| 204 | $\begin{matrix}CH_3\\|\\-CHCOOC_2H_5\end{matrix}$ | 135-143 (decomposition) | 1.26 (3H, t) 1.28 (6H, s) 1.43 (3H, d) 4.15 (5H, m) 4.80 (H, d, 3Hz) 4.86 (H, q) |
| 205 | $-CH_2COOC_4H_9$ | 60 | 0.92 (3H, m) 1.29 (6H, s) 1.52 (4H, m) 4.20 (5H, m) 4.64 (2H, s) 4.78 (H, d, 3Hz) |
| 206 | $-CH_2COCH_3$ | 89 | 1.24 (6H, s) 2.09 (3H, s) 4.10 (3H, m) 4.55 (2H, s) 4.80 (H, d, 2Hz) |

Preparation Example 2

Preparation of Novel Ascorbic Acid Derivative (Ia) Wherein X is Two Hydrogen Atoms (1) Synthesis of L-3-O-benzyl-2-O-methylcarbomethylascorbic Acid In 10 ml of tetrahydrofuran and 4 ml of methanol, was dissolved 2.15 g of L-3-O-benzyl-5,6-O-isopropylidene-2-O-methylcarbomethylascorbic acid obtained in (3) of Preparation example 1.

To the obtained solution, was added 6 ml of 2N-HCl, and the solution was stirred at room temperature for 20 hours.

The reaction solution was concentrated to about ½ of the total volume. To the concentrate, was added 5 ml of distilled water. The resulting solution was shaken with ethyl acetate (10 ml×2). Organic layers were combined, washed with saturated aqueous solution of sodium hydrogencarbonate and distilled water in the order mentioned, dried over sodium sulfate and concentrated under reduced pressure to provide an oily substance, which was then subjected to silica gel column chromatography and eluted with a mixture of benzene-ethyl acetate to afford 0.88g of the title compound L-3-O-benzyl-2-O-methylcarbomethylascorbic acid.

(2) Synthesis of L-3-O-methylcarbomethylascorbic Acid

In 5 ml of ethyl acetate, was dissolved 0.54 g of the compound obtained in (1). To the resulting solution, was added 0.10 g of 10% palladium-carbon powder. The obtained mixture was stirred in a hydrogen stream for 2 hours, and insoluble materials were filtered off. The filtrate was concentrated under reduced pressure and dried to afford the title compound L-2-O-methylcarbomethylascorbic acid (corresponding to compound No. 310 in Table-2).

Preparation Referential Example 2

Preparation of Other Ascorbic Acid Derivatives Included in the Ascorbic Acid Derivative (IA) Wherein X is Two Hydrogen Atoms Procedures were followed in the same manner as in Preparation example 2 to provide ascorbic acid derivatives designated as compound Nos. 301, 302, 303, 304, 305, 306, 307, 308 and 309 in Table-2.

TABLE 2

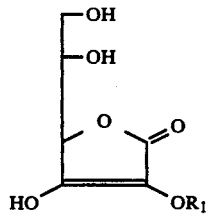

| Compound No. | $R_1$ | mp (°C.) | 90 mHz - NMR δ value |
|---|---|---|---|
| 301 | $-(CH_2)_{17}CH_3$ | 128-130 | 0.84 (3H, m) 1.23 (32H, m) 3.39 (2H, m) 3.72 (3H, m) 4.75 (H, d, 1Hz) |
| 302 | $-(CH_2)_{11}CH_3$ | 127-128 | 0.86 (3H, m) 1.20 (18H, m) 3.42 (2H, m) 3.82 (3H, m) 4.74 (H, d, 1Hz) |
| 303 | $-(CH_2)_7CH_3$ | 118-119 | 0.88 (3H, m) 1.26 (12H, m) 3.41 (2H, m) 3.82 (3H, m) 4.77 (H, d, 1Hz) |

TABLE 2-continued

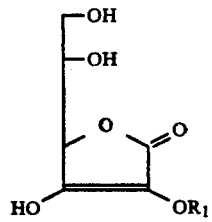

| Compound No. | R₁ | mp (°C.) | 90 mHz - NMR δ value |
|---|---|---|---|
| 304 | —(CH₂)₃CH₃ | (93)-105-110 | 0.89 (3H, m) 1.45 (4H, m) 3.42 (2H, m) 3.85 (3H, m) 4.76 (H, d, 1Hz) |
| 305 | —CH₂—C₆H₅ | 125-129 | 3.42 (2H, m) 3.77 (H, m) 4.76 (H, s) 4.96 (2H, s) 7.39 (5H, s) |
| 306 | —(CH₂)₃COOC₂H₅ | Oily substance | 1.21 (3H, t) 2.17 (2H, m) 2.47 (2H, t) 3.68 (2H, m) 4.01 (5H, m) 4.87 (H, d, 2Hz) |
| 307 | —(CH₂)₃COOH | Oily substance | 1.80 (2H, m) 2.40 (2H, t) 3.34 (2H, m) 3.78 (3H, m) 4.76 (H, s) |
| 308 | —CH(CH₃)—COOC₂H₅ | Oily substance | 1.19 (3H, t) 1.39 (3H, d) 3.39 (2H, m) 3.72 (H, m) 4.12 (2H, q) 4.77 (H, s) 4.80 (H, q) |
| 309 | —CH₂COOC₄H₉ | 34 | 0.88 (3H, t) 2.41 (4H, m) 3.39 (2H, m) 3.72 (H, m) 4.10 (2H, t) 4.60 (2H, s) 4.77 (H, s) |
| 310 | —CH₂COCH₃ | Oily substance | 2.13 (3H, s) 3.42 (2H, m) 3.72 (H, m) 4.55 (2H, s) 4.79 (H, s) |

Test Example 1 (Antioxidant Action Examined by Using Stable Free Radicals)

Reduction activity of α,α-diphenyl-β-picrylhydrazyl (DPPH) which was a stable free radical was examined according to the M. S. Blois method (nature, vol. 181, page 1199, 1958) and used as an index to antioxidant action. Thus, specimens were added to 3 ml of a 1 mM DPPH solution in ethanol, and absorbance at a wavelength of 517 nm was measured using a spectrophotometer after 20 minutes. The difference in absorbance from the solvent control [0.5% or less of dimethylformamide (DMF)]was taken as the reduction activity.

The 50% radical eliminating concentrations for the test compounds are shown in Table-3.

As can be seen from Table-3, the tested compounds of this invention were found to have improved antioxidant action.

TABLE-3

| Compound No. | 50% radical eliminating concentration |
|---|---|
| 201 | 1.4 × 10⁻⁵ M |
| 202 | 1.6 |
| 203 | 2.8 |
| 204 | 2.5 |
| 205 | 3.0 |
| 206 | 1.4 |
| 301 | 2.8 |
| 302 | 2.6 |
| 303 | 2.6 |
| 304 | 1.7 |
| 305 | 2.9 |
| 306 | 2.9 |
| 307 | 3.3 |
| 308 | 2.5 |
| 309 | 2.8 |
| 310 | 1.7 |

Test Example 2 (Effects on Formazan Formation in the Xanthine-xanthine Oxidase-Nitrotetrazolium Blue System)

Specimens were added to a 0.05 M phosphoric acid buffer solution (pH 7.8) containing xanthine, EDTA 2Na and Nitrotetrazolium Blue (NTB) so as to provide the respective final concentrations of $5 \times 10^{-5}$ M, $1 \times 10^{-4}$ M and $5 \times 10^{-4}$ M and warmed at 30° C. for 30 minutes. Xanthine oxidase (manufactured by Sigma Corp.) was added, and the resulting mixtures were warmed at 30° C. for 10 minutes to colorimetrically determine formazan formed by superoxide anion radicals. The inhibition ratio of formazan formation was determined from the results at concentrations of 0.5 mM and 4 mM of each specimen.

Results Are Shown in Table-4.

As can be seen from Table-4, tested compound Nos. 201 and 206 of this invention remarkably inhibited formazan formation and therefore the compound of this invention has improved ability to eliminate superoxide anion radicals.

TABLE 4

| Compound | Concentration (mM) | Inhibition ratio (%) of formazan formation |
|---|---|---|
| 201 | 0.5 | 9.1 |
|  | 4 | 19.1 |

TABLE 4-continued

| Compound | Concentration (mM) | Inhibition ratio (%) of formazan formation |
|---|---|---|
| 206 | 0.5 | 17.8 |
|  | 4 | 55.5 |

As detailed above, this invention provides a novel ascorbic acid derivative having excellent antioxidant action, particularly eliminating action on superoxides and a process for preparing the same.

Furthermore, this invention also provides a novel antioxidant comprising the aforementioned novel ascorbic acid derivative or other known ascorbic acid derivatives.

What is claimed is:

1. An ascorbic acid derivative represented by the formula:

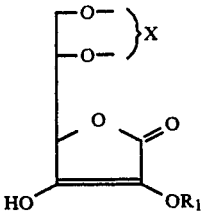

(Ia)

wherein $R_1$ is $-CH_2-CO-CH_3$ and $-CH_2-CO-C_2H_5$ and X represents two hydrogen atoms or $=C(CH_3)_2$.

2. The compound of claim 1, in which $R_1$ is $-CH_2-CO-CH_3-$.

3. The compound of claim 2, in which X is two hydrogen atoms.

4. The compound of claim 2, in which X is $=C(CH_3)_2$.

5. The compound of claim 1, in which $R_1$ is $-CH_2-CO-C_2H_5$.

6. The compound of claim 5, in which X is two hydrogen atoms.

7. The compound of claim 5, in which $R_1$ is $=C(CH_3)_2$.

* * * * *